United States Patent
Scirica (12)

(10) Patent No.: US 8,257,634 B2
(45) Date of Patent: Sep. 4, 2012

(54) ACTUATION SLED HAVING A CURVED GUIDE MEMBER AND METHOD

(75) Inventor: Paul Scirica, Huntington, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 253 days.

(21) Appl. No.: 12/573,909

(22) Filed: Oct. 6, 2009

(65) Prior Publication Data

US 2011/0079937 A1 Apr. 7, 2011

(51) Int. Cl.
*B29C 45/00* (2006.01)
*A61B 17/68* (2006.01)

(52) U.S. Cl. .................................. 264/328.1; 227/175.1
(58) Field of Classification Search ............... 264/328.1; 227/175.1, 176.1
See application file for complete search history.

(56) References Cited

U.S. PATENT DOCUMENTS

| | | | |
|---|---|---|---|
| 2,311,643 A * | 2/1943 | Crosby | 227/128 |
| 3,762,847 A | 10/1973 | Deuter et al. | |
| 3,799,494 A | 3/1974 | McLean, Jr. | |
| 3,889,919 A | 6/1975 | Ladney, Jr. | |
| 5,087,193 A | 2/1992 | Herbert, Jr. | |
| 5,324,186 A | 6/1994 | Bakanowski | |
| 5,752,644 A * | 5/1998 | Bolanos et al. | 227/180.1 |
| 5,797,537 A | 8/1998 | Oberlin et al. | |
| 5,834,035 A | 11/1998 | Osada et al. | |
| 5,939,101 A | 8/1999 | Green | |
| 6,367,765 B1 | 4/2002 | Wieder | |
| 6,696,011 B2 | 2/2004 | Yun et al. | |
| 7,134,637 B2 | 11/2006 | Dubay | |
| 2004/0070205 A1 | 4/2004 | Thomas et al. | |
| 2006/0068136 A1 | 3/2006 | Kinjou et al. | |
| 2007/0075115 A1 | 4/2007 | Olson et al. | |
| 2007/0194079 A1 | 8/2007 | Hueil et al. | |
| 2008/0082124 A1 | 4/2008 | Hess et al. | |
| 2009/0115105 A1 * | 5/2009 | Czernik et al. | 264/328.9 |

FOREIGN PATENT DOCUMENTS

| | | |
|---|---|---|
| DE | 3413113 A1 | 10/1984 |
| EP | 0931512 A | 7/1999 |
| EP | 1759812 A1 | 3/2007 |
| EP | 1772105 A1 | 4/2007 |
| EP | 2058105 A1 | 5/2009 |

OTHER PUBLICATIONS

Erhard, Gunter, Designing With Plastics, Hanser Publishers, 2006, pp. 239-274, 387-409.*
Campo, E. Alfredo, The Complete Part Design Handbook for Injection Molding of Thermoplastics, Hanser Publishers, 2006, pp. 211-223.*

(Continued)

*Primary Examiner* — Jill Heitbrink (57) ABSTRACT

An apparatus for injection molding includes at least one mold part having at least one surface. The mold part includes at least one mold part having at least one substantially central, sloping, non-linear surface, the at least one mold part including at least one shaped portion. The mold part further includes at least one substantially closed cavity region disposed within the at least one substantially central, sloping, non-linear surface. The mold part further includes at least one gate disposed on a base portion of the mold part for providing fluid communication to the at least one cavity region, the base portion having a plurality of recesses/depressions extending longitudinally along the length of the mold part. Additionally, at least one flow restrictor may be positioned on the mold part for initially directing flow of injected fluid to the at least one shaped portion.

12 Claims, 5 Drawing Sheets

OTHER PUBLICATIONS

European Search Report for EP 10251739.8-2307 date of completion is Dec. 29, 2010 (2 pages).

European Search Report for EP 08253617.8-2307 date of completion was Mar. 10, 2009 (3 pages).

* cited by examiner

# ACTUATION SLED HAVING A CURVED GUIDE MEMBER AND METHOD

BACKGROUND

1. Technical Field

The present disclosure relates to a method, an apparatus and a system to manufacture an actuation sled and, more particularly, to a mold for injection molding of an actuation sled.

2. Background of Related Art

Injection molding is a manufacturing process for producing parts and components. This process typically consists of inserting a molding material into an open rigid mold. The mold may be formed by halves. Typically, injection molding incorporates stationary and ejector mold halves, which open and close, to define a cavity where the molding or casting material is injected. Stationary mold halves are generally mounted to stationary platens. Ejector mold halves, in contrast, are capable of moving relative to stationary holder blocks for opening and closing the cavity. Ejector mold halves are mounted to ejector platens, which are generally connected to hydraulic actuators for providing movement. The stationary mold and the ejector mold are generally clamped together before the molding material has been injected into the cavity. After a suitable curing cycle, the mold is separated from the formed product. A successful injection molding process produces a part or a product substantially shaped as the mold.

The injection molding process, however, does not necessarily produce flawless products. The quality of the manufactured product is occasionally compromised by shortcomings during the injection molding process. For instance, gas within the molding cavity can substantially diminish the quality of the final product. Vacuum assistance has been used to address this issue and improve product quality. The general purpose of the vacuum assistance is to improve the production of injection molding by removing gases from within the molding cavities. Ideally, vacuum assisted injection molding produces parts with a reduced level of porosity and greater physical characteristics.

The physical characteristics of a molded article can also be improved by positioning vents on the molds. These vents release gases that otherwise would be trapped within the mold cavity. Consequently, vents reduce the occurrence of defective articles by minimizing incomplete mold cavity fillings. However, gases within the molding cavity are not the only cause of low quality products during the injection molding process. Occasionally, molding material is not uniformly distributed within the mold cavity. Thus, there is a need for a method, system, and apparatus for evenly distributing molding material throughout the mold cavity during an injection molding process.

Medical devices manufacturers often employ injection molding to produce certain components of surgical instruments. For example, some parts of surgical staplers are manufactured using injection molding. In particular, actuation sleds can be made by injecting molding material into a mold cavity. Actuation sleds serve to drive staple pushers vertically and, thus, eject staples. Actuation sleds typically include spaced apart ramps or cam wedges. These cam wedges are designed to cooperate with angular surfaces of the staple pushers to eject the staples. The angular surface of the staple pushers and the cam wedges complement each other. The cooperation between the angular surfaces of staple pushers and the actuation sled is a key step of the surgical stapling process. Hence, actuation sleds should have cam wedges with the least amount of imperfections. It is thus desirable to develop an apparatus, system, and method to manufacture high quality actuation sleds.

SUMMARY

The present disclosure relates to an apparatus for injection molding. The apparatus includes at least one mold having at least one substantially central, sloping, non-linear surface, the at least one mold part including at least one shaped portion. The apparatus further includes at least one substantially closed cavity region disposed within the at least one substantially central, sloping, non-linear surface. The apparatus further includes at least one gate disposed on a base portion of the mold part for providing fluid communication to the at least one cavity region, the base portion having a plurality of recesses extending longitudinally along the length of the mold part. The apparatus further includes at least one flow restrictor positioned on the mold part for initially directing flow of injected fluid to the at least one shaped portion.

A method for manufacturing an actuation sled is also disclosed herein. The method comprises the steps of forming at least one mold part having at least one substantially central, sloping, non-linear surface, the at least one mold part including at least one shaped portion, forming at least one substantially closed cavity region disposed within the at least one substantially central, sloping, non-linear surface, forming at least one gate disposed on a base portion of the mold part for providing fluid communication to the at least one cavity region, the base portion having a plurality of recesses extending longitudinally along the length of the mold part and forming at least one flow restrictor positioned on the mold part for initially directing flow of injected fluid to the at least one shaped portion.

BRIEF DESCRIPTION OF THE DRAWINGS

Various embodiments of the presently disclosed apparatus will be described hereinbelow with reference to the drawings wherein.

DETAILED DESCRIPTION OF THE EMBODIMENTS

The embodiments of the presently disclosed apparatus will now be described in detail with reference to the drawings in which like reference numerals designate identical or similar elements in each of the several views. As used herein and as is traditional, the term "distal" refers to the portion that is farthest from the user while the term "proximal" refers to the portion that is closest to the user. In addition, terms such as "above," "below," "forward," "rearward," "upper," "lower," etc. refer to the orientation of the figures or the direction of components and are simply used for convenience of description. As used herein a singular term generally includes the plural, and a plural term generally includes the singular unless otherwise indicated.

Injection molding typically entails the use of a mold. Most molds have a substantially closed cavity region. During the injection molding process, heated or melted molding material/fluid is introduced into the cavity region of the mold. This material should be rapidly injected to the cavity region at a substantially uniform and constant rate to inhibit premature curing of the material or incomplete filling of the molding cavity. The mold design should facilitate the flow of the molding material throughout the cavity region of the mold. The molding material should especially fill the essential sections of the mold.

Medical device manufacturers often use injection molding to make actuation sleds of surgical stapling instruments. Actuation sleds are typically used to drive staple pushers and thereby deploy staples disposed in a cartridge. Actuation sleds can include several shaped portions. For instance, a specific kind of actuation sled includes a base, a first camming member, a second camming member, and a guide member. First and second camming members may include respective first cam wedges and respective second cam wedges. Moreover, molds used to make actuation sleds substantially mirror the shape of the sleds. Accordingly, a mold adapted to produce an actuation sled can include a base, a first camming member, a second camming member, and a guide member. If the desired actuation sled has cam wedges, the mold should also have cam wedges.

In the present disclosure, the injection molding apparatus or actuation sled is designed with a substantially curved or substantially central, sloping, non-linear guide member (or rib) intended to control the speed of the injected molten plastic/material/fluid to ensure complete filling of the cavities located within the camming members. Additionally, in the present disclosure, the base portion of the injection molding apparatus or actuation sled includes a plurality of recesses, such recesses configured to construct a waffle shaped bottom coring that contribute to proper filling by minimizing warping and shrinkage (or sinks).

Figure 1:
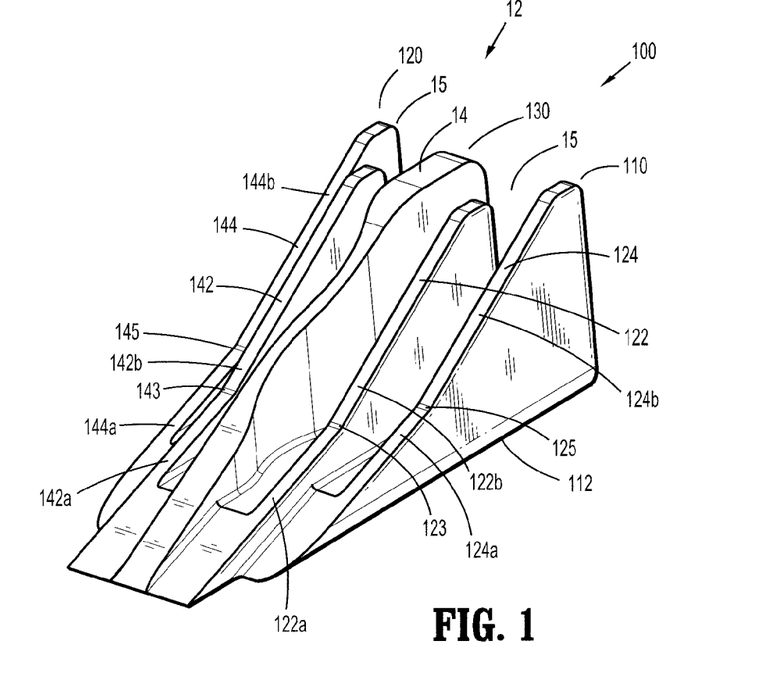
FIG. 1 is a perspective view of an injection molding apparatus, in accordance with an embodiment of the present disclosure.

With reference to FIG. 1, a perspective view of an injection molding apparatus, in accordance with an embodiment of the present disclosure is presented.

The injection molding apparatus, according to an embodiment of the present disclosure, is shown generally as 100. The apparatus 100 includes at least one mold part 12 having at least one surface 14. Surface 14 extends the periphery of apparatus 100. The mold part 12 has at least one shaped portion 15 and can be made of a polymer such as polyphtalamide. Although the drawings depict a mold part 12 having specific kinds of shaped portions 15, the present disclosure envisions mold parts having shaped portion 15 with different shapes. The configuration of shaped portions 15 used with apparatus 100 is determined by the configuration of the finished product.

In the embodiment shown in FIG. 1, mold part 12 has a plurality of shaped portions 15. In particular, mold part 12 includes a base 112, a first camming member 110, a second camming member 120, and a guide member 130. At least a portion of base 112 contacts first camming member 110, second camming member 120, and guide member 130.

Guide member 130 is disposed between first and second camming members 110, 120 and is laterally spaced apart from camming members 110, 120. Guide member 130 extends vertically from base 112. While the depicted embodiments show a guide member 130 having a particular spatial configuration with respect to base 112 and camming members 110, 120, the present disclosure envisions guide members having other suitable configurations. Ultimately, the configuration of guide member 130 is determined by the configuration of the finished product.

Guide member 130 is depicted as a curved member or as a substantially central, sloping, non-linear surface or member extending the length of the apparatus 100. The width of the guide member 130 varies as it extends longitudinally along the length of the apparatus 100. The substantially central, sloping, non-linear guide member 130 aids in the controlling of the speed and direction of the injected plastic/material/liquid received via the one or more gates 152, 154 (see FIG. 1B).

Moreover, first and second camming members 110, 120 also extend vertically from base 112. Each camming member 110, 120 includes respective first cam wedge 122, 142 and second cam wedge 124, 144. Cam wedges 122, 124, 142, 144 have substantial triangular cross-sectional areas. The shapes of cam wedges 122, 124, 142, 144, however, ultimately depend on the desired shape of the cam wedges of the actuation sled. Thus, the present disclosure contemplates many other cam wedges having different shapes and sizes. As shown in FIG. 1, first cam wedges 122, 142 are laterally spaced apart from second cam wedges 124, 144, respectively. In addition, first cam wedges 122, 142 include respective upper portions 122*u*, 142*u* and respective lower portions 122*l*, 142*l* (see FIG. 1B). Similarly, second cam wedges 124, 144 include respective upper portions 124*u*, 144*u* and lower portions 124*l*, 144*l*.

Figure 1A:
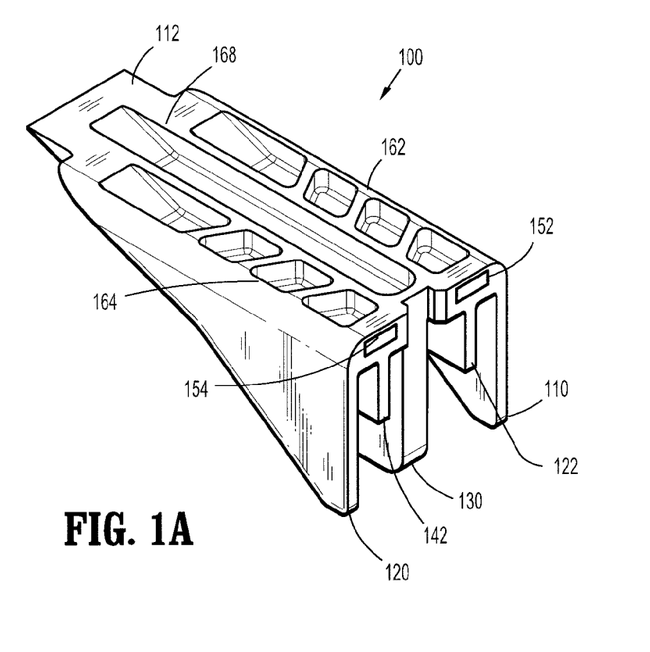
FIG. 1A is a bottom elevational view of the injection molding apparatus illustrated in FIG. 1, in accordance with the present disclosure.
Figure 1B:
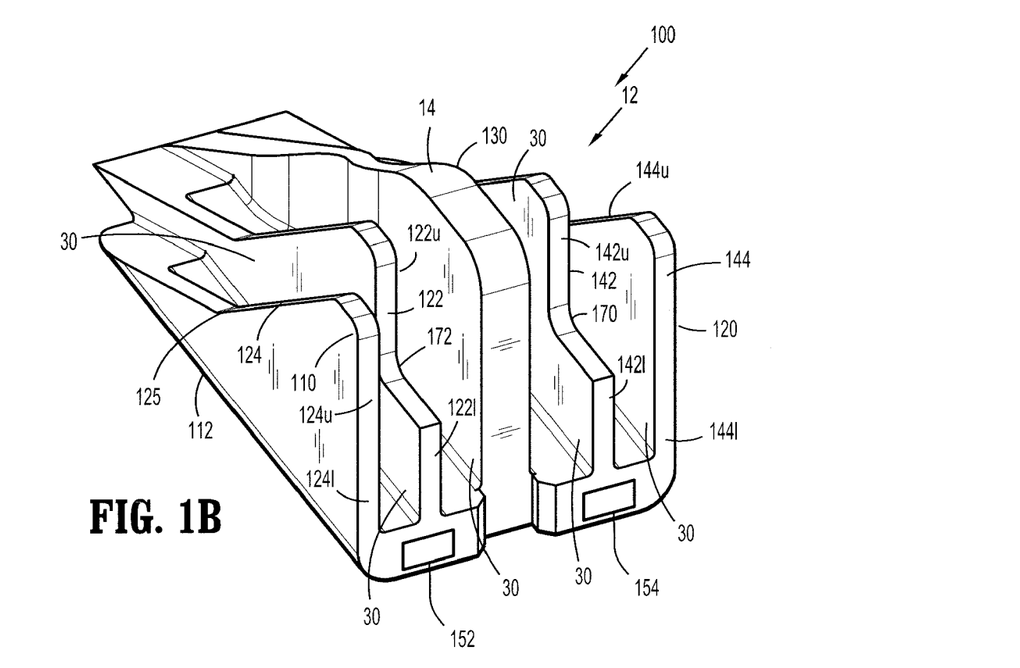
FIG. 1B is a rear elevational view of the injection molding apparatus illustrated in FIG. 1, in accordance with the present disclosure.

With reference to FIGS. 1 and 1B, the upper portions 122*u* and 142*u* of first cam wedges 122, 142 include respective first drive faces 122*a*, 122*b*, 142*a*, and 142*b*. First drive faces 122*a*, 142*a* define first drive angles on camming members 110, 120 with respect to base 112 of apparatus 100. As seen in FIGS. 1, 3, 4, and 5, transition points 123, 143 are disposed at the intersection of first and second drive faces 122*a*, 142*a*, and 122*b*, 142*b*, respectively. A plane X extending through transition points 123, 143 is substantially parallel to base 112 (see FIGS. 3 and 6). Second drive faces 122*b*, 142*b* define respective second drive angles on camming member 110, 120 with respect to plane X.

Similarly, second cam wedges 124, 144 include respective drive faces 124, 144 include respective first and second drive faces 124*a*, 124*b*, 144*a*, and 144*b*. First drive faces 124*a*, 144*a* define first drive angles on camming surfaces 110, 120 with respect to base 112. As seen in FIGS. 1, 3, 4, and 5, transition point 125, 145 are positioned at the intersection of first and second drive faces 124*a*, 124*b* and 144*a* and 144*b*. Plane X extends through transition points 125, 145 and is substantially parallel to base 112. Second drive faces 124*b*, 144b define respective second drive angles on camming members 110, 120 with respect to plane X.

With reference to FIG. 1A, a bottom elevational view of the injection molding apparatus illustrated in FIG. 1, in accordance with the present disclosure is presented.

Apparatus 100 includes gates 152, 154 for providing fluid communication to the cavity region 30 (see FIGS. 1B and 5) of mold part 12. In use, an external source of injection molding material supplies an interstitial mass to the cavity region 30 of the mold part 12 through gates 152, 154. Gates 152, 154 can have any suitable shape. In the depicted embodiment, gates 152, 154 are disposed on the base 112 of mold part 12. Specifically, gates 152, 154 are located on a proximal portion of base 112, as shown in FIGS. 1A and 1B. Alternatively, a gate or a plurality of gates can be located anywhere on the part.

Additionally, apparatus 100 depicts the base 112 of the injection molding apparatus 100 or actuation sled including a plurality of recesses/depressions 162, 164, 168, such recesses 162, 164, 168 configured to construct a waffle shaped bottom coring that contribute to proper filling by minimizing warping and shrinkage (or sinks). The plurality of recesses 162, 164, 168 will be further described with reference to FIG. 2 below.

With reference to FIG. 1B, a rear elevational view of the injection molding apparatus illustrated in FIG. 1, in accordance with the present disclosure is presented.

The rear view 100 clearly illustrates the upper portions and the lower portions of the cam wedges 122, 124, 142, 144. For example cam wedge 122 has an upper portion 122u and a lower portion 122l, cam wedge 124 has an upper portion 124u and a lower portion 124l, cam wedge 142 has an upper portion 142u and a lower portion 142l, and cam wedge 144 has an upper portion 144u and a lower portion 144l. Additionally, the second cam wedge 142 of the first camming member 110 includes a transition point 172 and the second cam wedge 122 of the second camming member 120 includes a transition point 170. Also, as clearly seen in FIG. 3, the first cam wedge 122 and the second cam wedge 124 of the first camming member 110 are offset with respect to each other. Similarly, the first cam wedge 142 and the second cam wedge 144 of the second camming member 120 are offset with respect to each other.

In operation, during the injection molding process, an external source of heated or melted injection molding material/plastic/fluid supplies cavity region 30 (see FIG. 5) of mold part 12 with interstitial mass through gates 152, 154. Gates 152, 154, which are located at a proximal portion of base 112, provide the necessary fluid communication between the external source of injection molding material or fluid or plastic and cavity region 30 of mold part 12. As injection molding material is introduced into cavity region 30, flow restrictors 34 (see FIG. 4) initially direct the material to the upper portions 122a, 124a, 142a, 144a of the cam wedges 122, 124, 142, 144. After the upper portions upper portions 122a, 124a, 142a, 144a of the cam wedges 122, 124, 142, 144 are filled with interstitial mass, the remaining space inside the cavity region fills with interstitial mass. Once a suitable curing cycle has elapsed, the interstitial mass solidifies. This solid mass can then be extracted from mold part 12.

Figure 2:
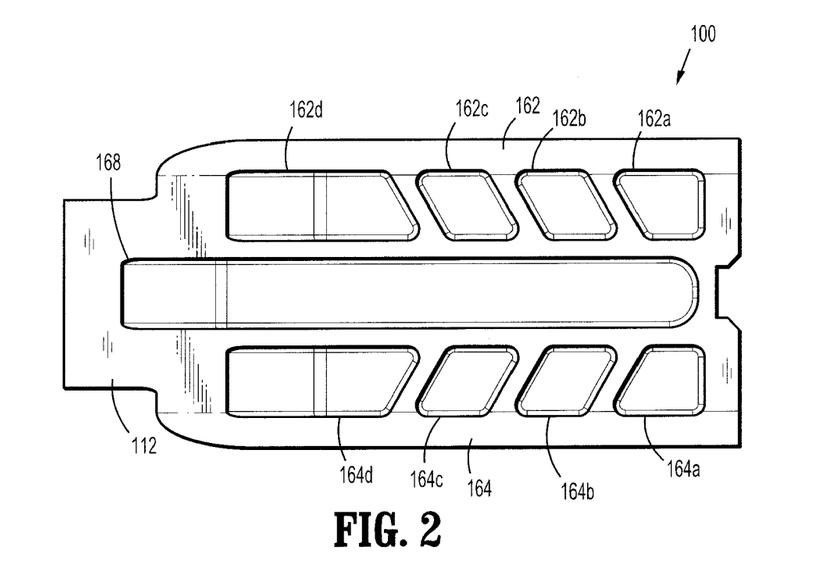
FIG. 2 is a bottom view of the injection molding apparatus illustrated in FIG. 1, in accordance with the present disclosure.

With reference to FIG. 2, a bottom view of the injection molding apparatus illustrated in FIG. 1, in accordance with the present disclosure is presented.

The bottom view 100 includes a plurality of recesses 162, 164, and 168 located on the base portion 112 of the apparatus 100. In this embodiment, the plurality of recesses 162 and 164 are opposed to each other and extend the length of the base portion 112. The recess 168 extends across the central length of the base 112. Moreover, in this exemplary embodiment, the plurality of recesses 162 consist of recesses 162a, 162b, 162c, 162d and the plurality of recesses 164 consist of recesses 164a, 164b, 164c, 164d. The plurality of recesses 162, 164, 168 may be any shape or size contemplated by one skilled in the art. The divot of each of the plurality of recesses 162, 164, 168 may be any depth contemplated by one skilled in the art. Additionally, the depth of the plurality of recesses 162, 164, 168 may be the same or may be different. In other words, the depth of the plurality of recesses 162 may be the same as the depth of the plurality of recesses 164, but different than the depth of recess 168. Alternately, the depth of the plurality of recesses 162 may be different with respect to each other (i.e., 162a, 162b, 162c, 162d). Similarly, the depth of the plurality of recesses 164 may be different with respect to each other (i.e., 164a, 164b, 164c, 164d). One skilled in the art may contemplate a plurality of different structures and/or configurations and/or designs on the base 112.

Figure 3:
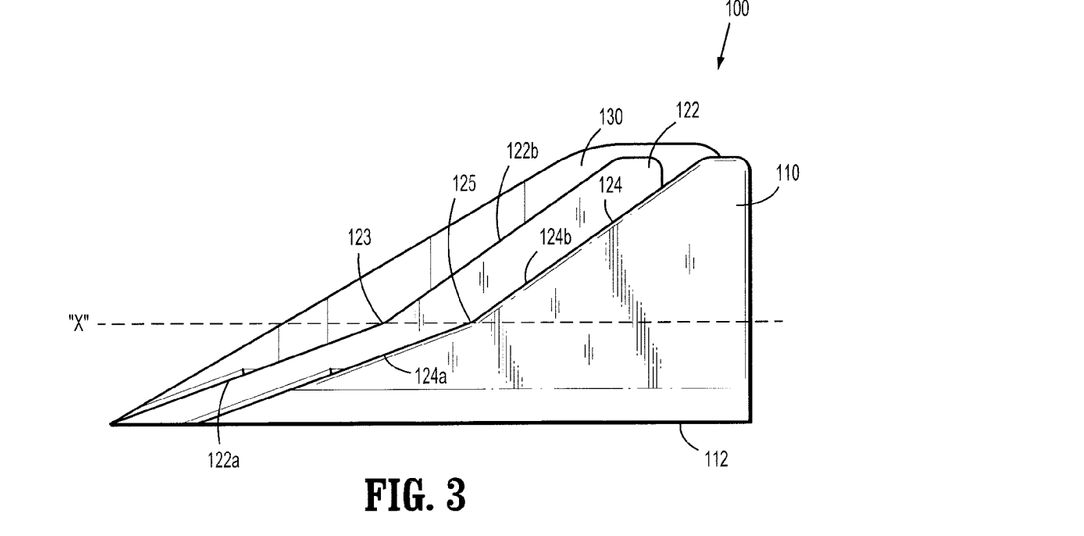
FIG. 3 is a side view of the injection molding apparatus illustrated in FIG. 1, in accordance with the present disclosure.

With reference to FIG. 3, a side view of the injection molding apparatus illustrated in FIG. 1, in accordance with the present disclosure is presented.

The side view 100 illustrates the first camming member 110, the first cam wedge 122 of the first camming member 110, the guide member 130, and the base portion 112. The first camming member 110 depicts the second cam wedge 124 having first and second drive faces 124a, 124b and transition point 125. The first camming member 110 further depicts the first cam wedge 122 having first and second drive faces 122a, 122b and transition point 123.

Figure 4:
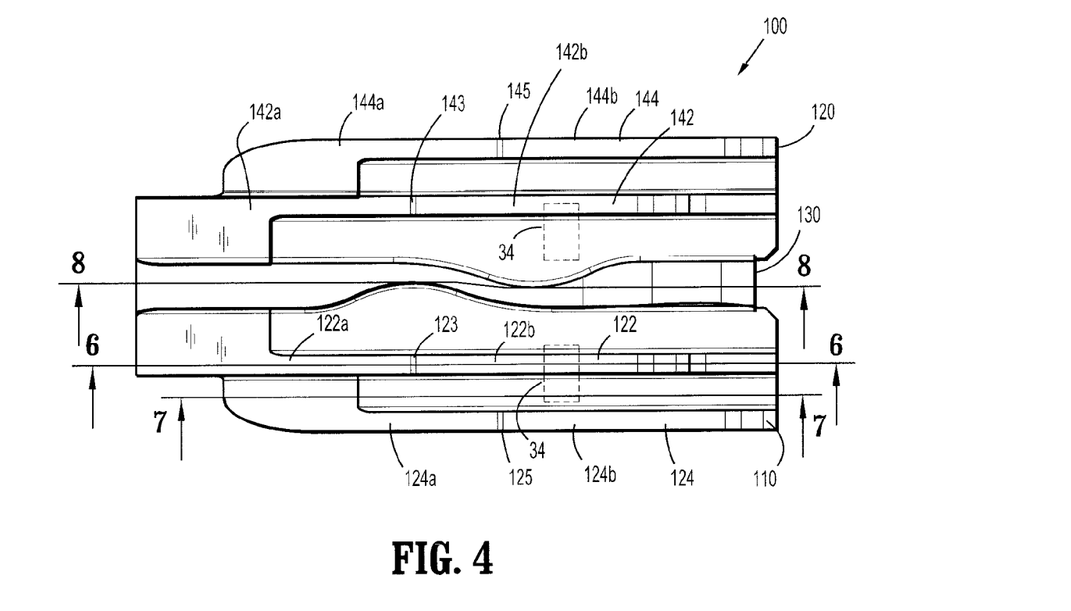
FIG. 4 is a top view of the injection molding apparatus illustrated in FIG. 1, in accordance with the present disclosure.

With reference to FIG. 4, a top view of the injection molding apparatus illustrated in FIG. 1, in accordance with the present disclosure is presented.

The top view 100 additionally includes at least one flow restrictor 34 positioned on the mold part 12 for initially directing flow of the interstitial mass to the upper portion 122u, 124u, 142u, 144u (see FIG. 1B) of cam wedges 122, 124, 142, 144. Alternatively, flow restrictors 34 can be configured to direct the flow of interstitial mass to any other suitable shaped portion 15. In the illustrated embodiment, apparatus 100 includes two flow restrictors 34 longitudinally spaced apart from gates 152, 154 (see FIGS. 1A and 1B). Each flow restrictor 34 is disposed on the base 112 adjacent to a camming member 110, 120. The present disclosure, however, envisions that flow restrictors 34 can be positioned at any other suitable location.

Flow restrictors 34 may have a substantially rectangular shape but other suitable shapes are also contemplated in the present disclosure. Each flow restrictor 34 can consist of an indentation. Regardless of flow restrictors 34 structure, flow restrictors 34 are adapted to direct flow of the interstitial mass to a shaped portion 15 of mold part 12. In doing so, flow restrictors 34 promote even distribution of the interstitial mass throughout cavity region 30 (see FIG. 5). In one embodiment, flow restrictors 34 are specifically configured to initially direct flow of the interstitial mass to the upper portions 122u, 124u, 142u, 144u (see FIG. 1B) of cam wedges 122, 124, 142, 144. By initially directing flow to the upper portions 122u, 124u, 142u, 144u (see FIG. 1B) of cam wedges 122, 124, 142, 144, flow restrictors 34 facilitate uniform distribution of interstitial mass throughout cavity region 30.

Each flow restrictor 34 is strategically located relative to gates 152, 154 so that the molten plastic flow is directed towards the difficult areas of the cam wedges 122, 124, 142, 144 first, thereby assuring a more complete mold filling. This minimizes incomplete mold filling known as short shot that produces a defective sled part. In other words, each flow restrictor 34 acts as a flow director that directs the flow forwards towards the areas that are difficult to fill first and ensures a more complete mold filling. In case difficult areas are not filled first, the flow front may freeze, thus blocking the melt flow access and producing partially filled cam wedges, 122, 124, 142, 144. Incomplete cam wedges 122, 124, 142, 144 may result in not fully formed staples.

The benefit of flow restrictors 34 also permits cam wedges 122, 124, 142, 144 to be molded with a thin cross section, thus resulting in a sled part having a minimal footprint. The small sled part permits design of a SULU (Single Use Loading Unit) with a reduced cross-section, which is desirable for medical instruments that are used for minimally invasive medical procedures. Miniaturized medical instruments permit practitioners to perform procedures using minimally invasive techniques with their attendant advantages.

Figure 5:
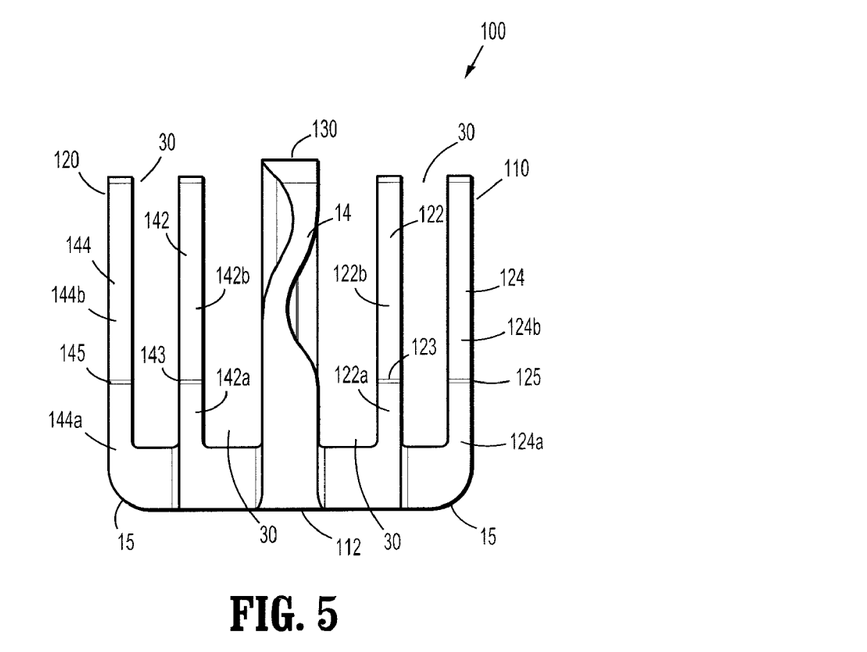
FIG. 5 is a front view of the injection molding apparatus illustrated in FIG. 1, in accordance with the present disclosure.

With reference to FIG. 5, a front view of the injection molding apparatus illustrated in FIG. 1, in accordance with the present disclosure is presented.

The front view 100 of apparatus 100 further includes at least one substantially closed cavity region 30 disposed within the surface 14. Cavity region 30 is designed for molding at least part of an interstitial mass. The shape of cavity region 30 substantially mirrors the shape of the shaped portions 15 of mold part 12 (see FIG. 1). Accordingly, in operation, the interstitial mass takes the shape of cavity region 30 to form an actuation sled or any other suitable product.

The front view 100 clearly illustrates the substantially central, sloping, non-linear member 130. The width of the guide member 130 varies as it extends the length of the apparatus 100. In certain embodiments, the upper and lower portions of the surface 14 may be a first width and the middle portion of the surface may be a second width, where the first width is greater than the second width. Of course, the width of the surface 14 may vary throughout the length of the guide member 130. One skilled in the art may contemplate a plurality of different widths along the length of the guide member 130 to achieve the advantages of the present disclosure.

Figure 6:
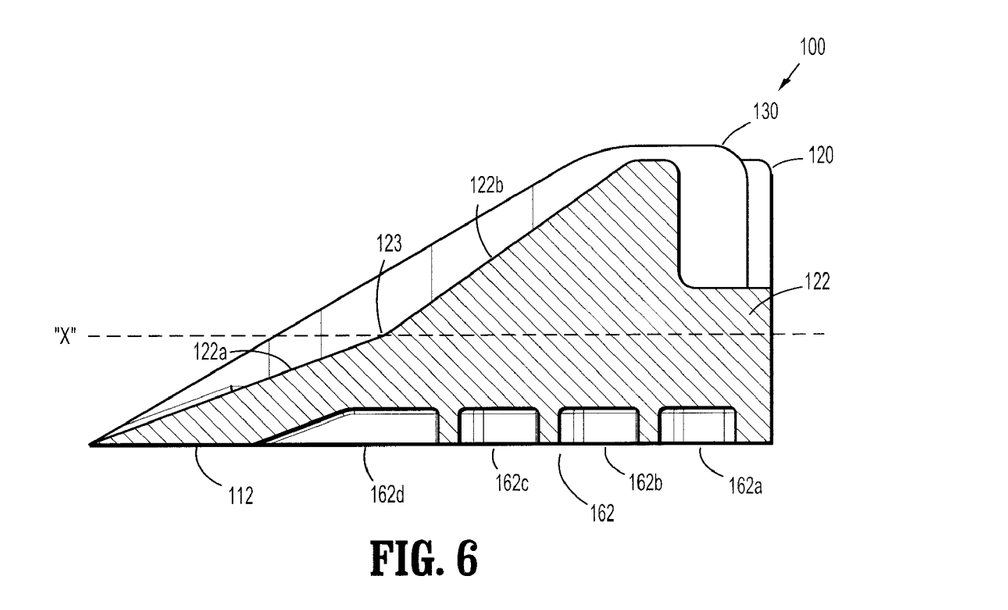
FIG. 6 is a cross-sectional view taken along section line 6-6 of FIG. 4, in accordance with the present disclosure.

With reference to FIG. 6, a cross-sectional view taken along section line 6-6 of FIG. 4, in accordance with the present disclosure is presented.

The cross-sectional view 100 depicts the second camming member 120, the first cam wedge 122 of the second camming member 120, the guide member 130, and the base portion 112. The second camming member 120 depicts the first cam wedge 122 having first and second drive faces 122a, 122b and transition point 123. Additionally, the cross-sectional view 100 illustrates the plurality of recesses/depressions 162 (e.g., 162a, 162b, 162c, 162d) when taken along section line 6-6. The height of the plurality of recesses 162 may be any desirable height based on desired application.

Figure 7:
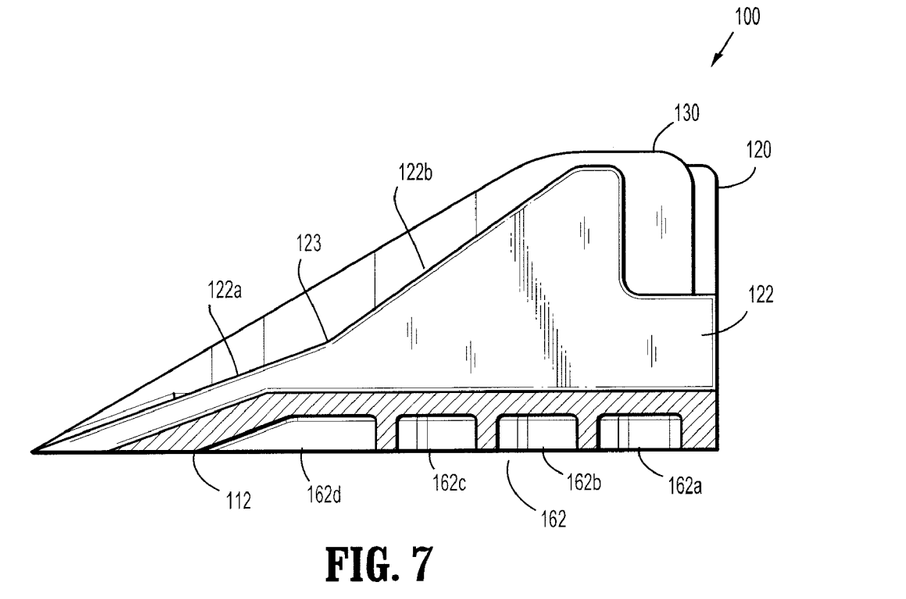
FIG. 7 is a cross-sectional view taken along section line 7-7 of FIG. 4, in accordance with the present disclosure.

With reference to FIG. 7, a cross-sectional view taken along section line 7-7 of FIG. 4, in accordance with the present disclosure is presented.

The cross-sectional view 100 depicts the second camming member 120, the first cam wedge 122 of the second camming member 120, the guide member 130, and the base portion 112. The second camming member 120 depicts the first cam wedge 122 having first and second drive faces 122a, 122b and transition point 123. Additionally, the cross-sectional view 100 illustrates the plurality of recesses 162 (e.g., 162a, 162b, 162c, 162d) when taken along section line 7-7. The height of the plurality of recesses 162 may be any desirable height based on desired application.

Figure 8:
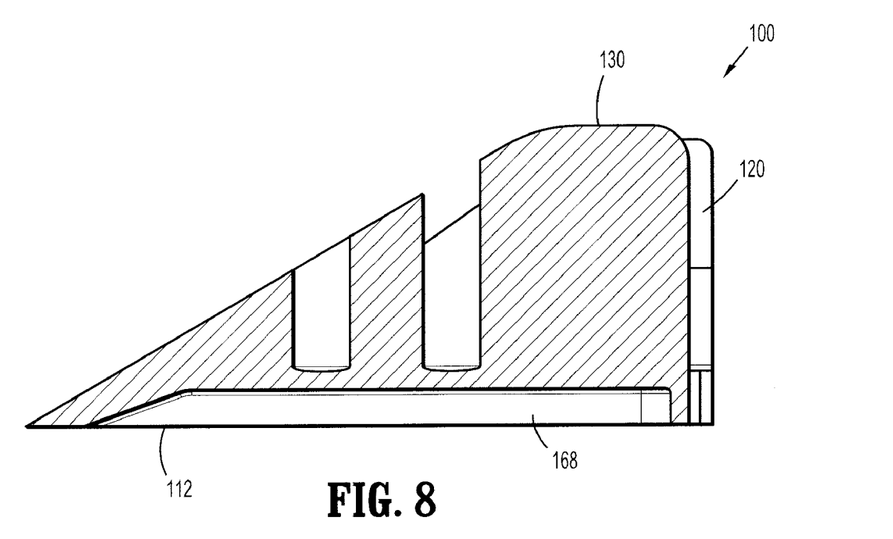
FIG. 8 is a cross-sectional view of the injection molding apparatus taken along section line 8-8 of FIG. 4, in accordance with the present disclosure.

With reference to FIG. 8, a cross-sectional view of the injection molding apparatus taken along section line 8-8 of FIG. 4, in accordance with the present disclosure is presented.

The cross-sectional view 100 depicts the second camming member 120, the guide member 130, and the base portion 112. Additionally, the cross-sectional view 100 illustrates the recess 168 when taken along section line 8-8. The height of the recess 168 may be any desirable height based on desired application.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure. For example, it is contemplated that the shaped portions of the mold part may define the shape of another component of a surgical instrument.

The invention claimed is:

1. A sled product formed in a mold, comprising:
   a guide member having a proximal end and a distal end, the proximal and distal ends having a first width, the guide member further having a single, centrally disposed portion between the proximal and distal ends, the centrally disposed portion including at least one shaped portion;
   the at least one shaped portion having a sloping, non-linear surface;
   wherein the centrally disposed portion has a second width different than the first width of the proximal and distal ends of the guide member; and
   wherein the at least one shaped portion includes a first camming member and a second camming member, the first and second camming members each having spaced apart first and second cam wedges, each of the cam wedges including at least first and second drive faces configured to define first and second drive angles with respect to a base portion of the sled product.

2. The sled product formed in the mold according to claim 1, wherein the spaced apart first and second cam wedges of each of the first and second camming members are offset with respect to each other.

3. The sled product formed in the mold according to claim 1, wherein the centrally disposed portion modifies a speed and a direction of the injected fluid received via the at least one gate due to a curved-shape configuration of a central wall of the guide member.

4. The sled product formed in the mold according to claim 1, wherein the at least one shaped portion includes an upper portion and a lower portion.

5. The sled product formed in the mold according to claim 1, wherein the sled product is made of a polymer.

6. The sled product formed in the mold according to claim 1, wherein the sled product is made of polyphtalamide.

7. A method comprising:
   injecting a polymer into a mold so as to form a guide member for the sled product, the mold being shaped so that:
   (i) the guide member has a proximal end and a distal end, the proximal and distal ends having a first width;
   (ii) the guide member has a single, centrally disposed portion between the proximal and distal ends, the centrally disposed portion further including at least one shaped portion;
   (iii) the shaped portion having a sloping, non-linear surface;
   (iv) wherein the centrally disposed portion has a second width different than the first width of the proximal and distal ends of the guide member; and
   (v) wherein the at least one shaped portion includes a first camming member and a second camming member, the first and second camming members each having spaced apart first and second cam wedges, each of the cam wedges including at least first and second drive faces configured to define first and second drive angles with respect to a base portion of the sled product.

8. The method according to claim 7, wherein the spaced apart first and second cam wedges of each of the first and second camming members are offset with respect to each other.

9. The method according to claim 7, wherein the centrally disposed portion modifies a speed and a direction of the injected fluid received via the at least one gate due to a curved-shape configuration of a central wall of the guide member.

10. The method according to claim 7, wherein the at least one shaped portion includes an upper portion and a lower portion.

11. The method according to claim 7, wherein the sled product is made of the polymer.

12. The method according to claim 7, wherein the sled product is made of polyphtalamide.

* * * * *